United States Patent
Gu et al.

(10) Patent No.: US 7,628,907 B2
(45) Date of Patent: Dec. 8, 2009

(54) GAS SENSOR

(75) Inventors: Yuandong Gu, Plymouth, MN (US); Barrett E. Cole, Bloomington, MN (US); Robert E. Higashi, Shorewood, MN (US)

(73) Assignee: Honeywell International Inc., Morristown, NJ (US)

( * ) Notice: Subject to any disclaimer, the term of this patent is extended or adjusted under 35 U.S.C. 154(b) by 749 days.

(21) Appl. No.: 11/162,060

(22) Filed: Aug. 26, 2005

(65) Prior Publication Data
US 2007/0045129 A1 Mar. 1, 2007

(51) Int. Cl.
*G01N 27/14* (2006.01)
*G01N 25/02* (2006.01)

(52) U.S. Cl. .............. 205/784; 205/785; 204/424; 374/10

(58) Field of Classification Search .............. 205/784, 205/785, 782; 204/421–429; 73/23.2, 29.01, 73/29.05, 31.05, 31.06; 374/10–14, 178, 374/179
See application file for complete search history.

(56) References Cited

U.S. PATENT DOCUMENTS

| | | | |
|---|---|---|---|
| 4,151,060 A | 4/1979 | Isenberg et al. | |
| 4,937,059 A | 6/1990 | Kolts et al. | |
| 5,124,021 A | 6/1992 | Kaneyasu et al. | |
| 5,397,541 A | 3/1995 | Post | |
| 5,434,551 A | 7/1995 | Chen et al. | |
| 5,448,905 A | 9/1995 | Stetter et al. | |
| 5,695,624 A | 12/1997 | Garzon et al. | |
| 6,006,582 A | 12/1999 | Bhandari et al. | |
| 6,144,285 A | 11/2000 | Higashi | |
| 6,200,445 B1 | 3/2001 | Yokota et al. | |
| 6,203,805 B1 | 3/2001 | Collins et al. | |
| 6,238,085 B1 * | 5/2001 | Higashi et al. | 374/10 |
| 6,254,749 B1 | 7/2001 | Yokota et al. | |
| 6,265,222 B1 | 7/2001 | DiMeo, Jr. et al. | |
| 6,325,905 B1 | 12/2001 | Matsui et al. | |
| 6,368,479 B1 | 4/2002 | Yokota et al. | |
| 6,447,658 B1 | 9/2002 | Wu et al. | |
| 6,468,407 B2 | 10/2002 | Clyde et al. | |
| 6,514,397 B2 | 2/2003 | LaBarge et al. | |
| 6,555,159 B2 | 4/2003 | Clyde et al. | |
| 6,579,435 B2 | 6/2003 | Wang et al. | |
| 6,579,436 B2 | 6/2003 | Wang et al. | |
| 6,585,872 B2 | 7/2003 | Donelon et al. | |

(Continued)

OTHER PUBLICATIONS

Kim et al., "Co2-sensing characteristics of SnO2 thick film by coating lanthanum oxide," Sensors and Actuators, B 62, pp. 61-66, 2000.

(Continued)

*Primary Examiner*—Kaj K Olsen
*Assistant Examiner*—Kourtney R Salzman
(74) *Attorney, Agent, or Firm*—Kris T. Fredrick (57) ABSTRACT

A gas sensor is provided for detecting one or more gases in a gas sample. The gas sensor includes a substrate, a solid electrolyte layer including lanthanum oxide for sensing carbon dioxide, a heating element thermally coupled to the solid electrolyte layer, and a controller coupled to the heating element and the solid electrolyte layer. The controller heats the heating element so that the solid electrolyte layer reaches an operating. Methods of sensing carbon dioxide and humidity are also disclosed.

11 Claims, 5 Drawing Sheets

U.S. PATENT DOCUMENTS

| | | |
|---|---|---|
| 6,709,558 B2 | 3/2004 | LaBarge et al. |
| 6,723,217 B1 | 4/2004 | Duce et al. |
| 6,793,788 B2 | 9/2004 | Wang et al. |
| 6,797,138 B1 | 9/2004 | Detwiler et al. |
| 6,800,158 B2 | 10/2004 | Polikarpus et al. |
| 6,916,384 B2 | 7/2005 | Jain et al. |
| 6,922,639 B2 | 7/2005 | Kawase et al. |
| 2004/0084308 A1 | 5/2004 | Cole et al. |
| 2004/0158410 A1 | 8/2004 | Ono et al. |
| 2005/0019578 A1 | 1/2005 | Bosteels |
| 2005/0230246 A1 | 10/2005 | Lemaster et al. |
| 2005/0230250 A1 | 10/2005 | Imamura et al. |
| 2005/0241136 A1 | 11/2005 | Wu et al. |

OTHER PUBLICATIONS

Watson et al., "A Differential Scanning Calorimeter for Quantitative Differential Thermal Analysis," vol. 36, No. 7, pp. 1233-1238, Jun. 1964.

* cited by examiner

GAS SENSOR

BACKGROUND OF THE INVENTION

This invention generally relates to gas sensors, and more specifically, to gas sensors for detecting one or more gases in a sample of an environment or flow stream.

There is growing interest in monitoring and controlling air quality in both indoor and outdoor environments, including carbon dioxide concentration. There are several types of gas sensors that can monitor carbon dioxide ($CO_2$) or other gases.

SUMMARY OF THE INVENTION

The present invention is directed toward a gas sensor, and more specifically, a gas sensor for detecting carbon dioxide and other gases in a gas sample, and in some cases humidity. The gas sensor includes a sensor for sensing a desired gas and a heater for heating the sensor. During operation, a controller provides power to the heater to heat the sensor to an operating temperature, which is above ambient temperature. In some embodiments, the sensor and heater are thermally isolated from some or all of the remainder of the sensor, such as the sensor substrate. This may help reduce the amount of power that is required to heat the heater and sensor to the operating temperature. This may make it more energy efficient to heat the sensor to an operating temperature at spaced time intervals. The gas sensor of the present invention may be ideally suited for battery powered and/or wireless applications.

Methods of sensing a gas are also disclosed. One illustrative method includes the steps of providing a solid electrolyte layer including lanthanum oxide, contacting the solid electrolyte layer with a gas sample, heating the solid electrolyte layer from 100 degrees Celsius to an operating temperature with a first amount of energy, and determining a concentration of carbon dioxide in the gas sample based on first amount of energy.

Another illustrative method includes the steps of providing a solid electrolyte layer including lanthanum oxide, contacting the solid electrolyte layer with a gas sample, heating the solid electrolyte layer to about 100 degrees Celsius with a water desorbing amount of energy, heating the solid electrolyte layer from about 100 degrees Celsius to a carbon dioxide desorbing temperature with a carbon dioxide desorbing amount of energy, and then determining a humidity level in the gas sample based on the water desorbing amount of energy and determining a concentration of carbon dioxide in the gas sample based on the carbon dioxide amount of energy.

DETAILED DESCRIPTION OF THE INVENTION

Figure 1:
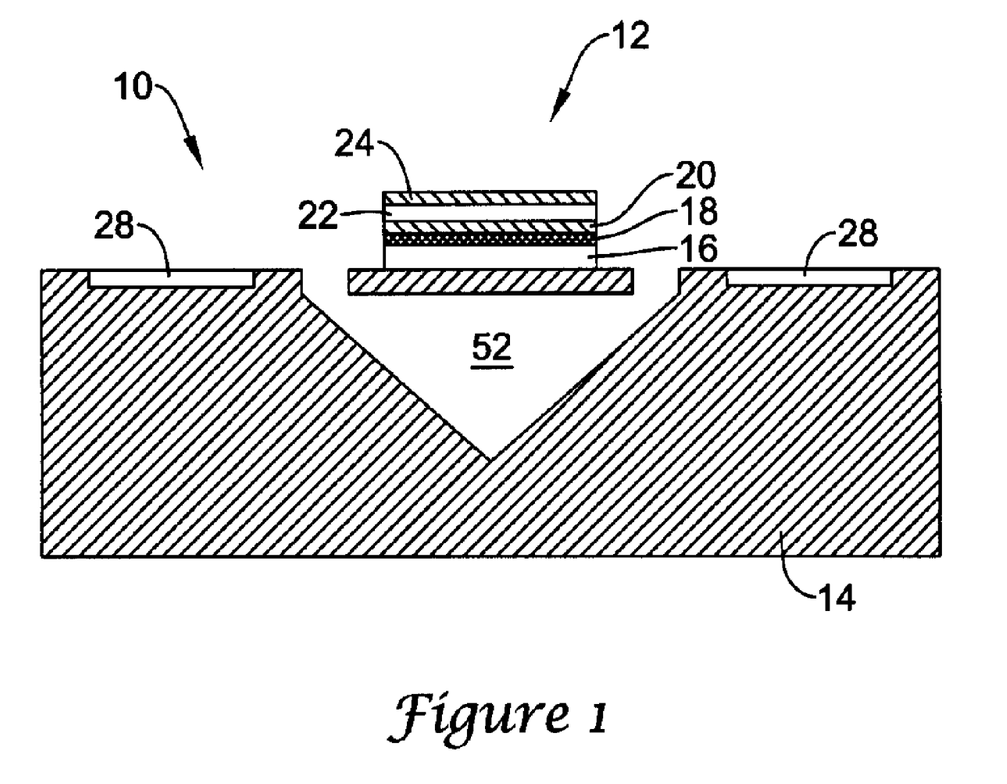
FIG. 1 is a cross-sectional side view of an illustrative gas sensor in accordance with the present invention.
Figure 2:
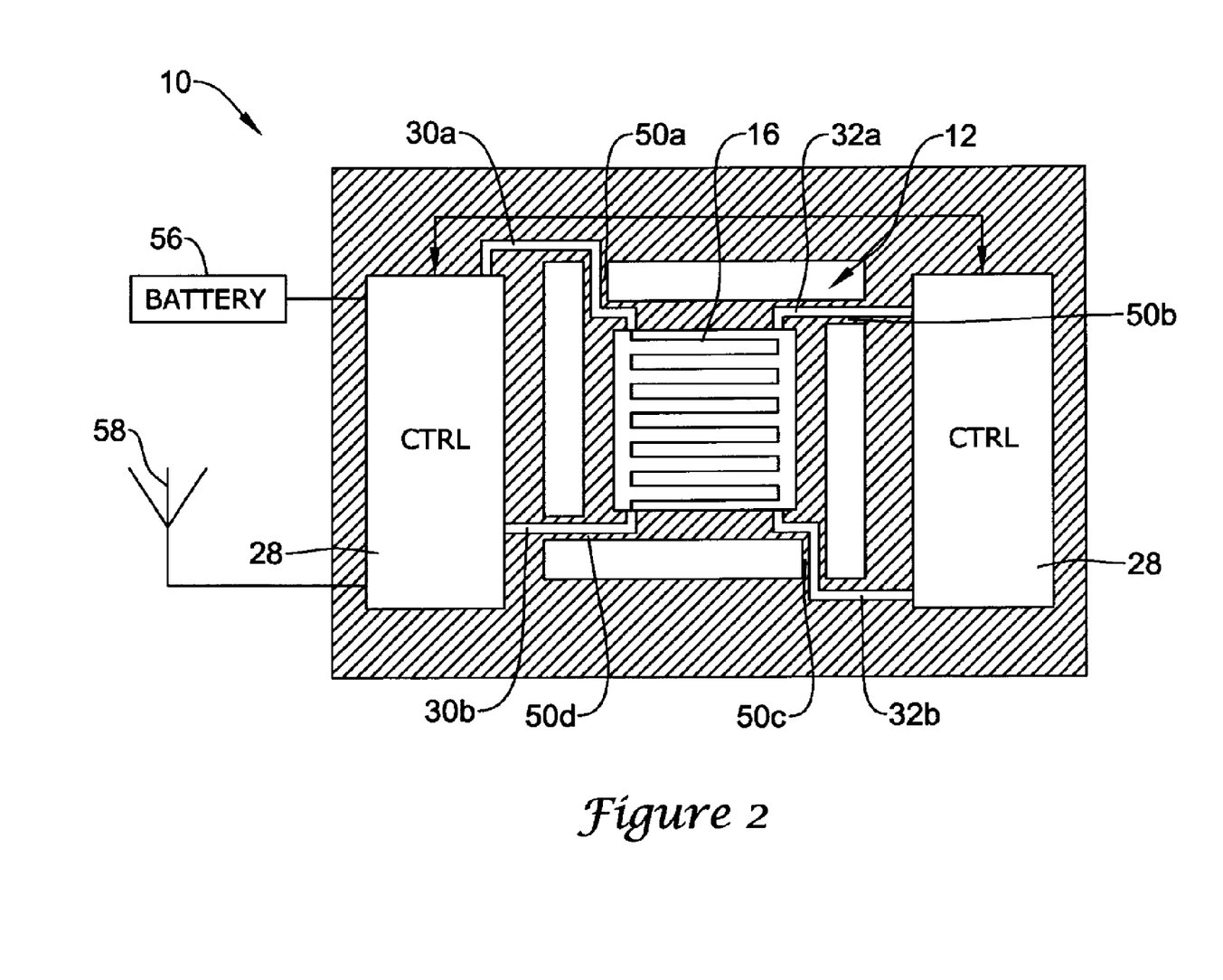
FIG. 2 is a schematic top view of the illustrative gas sensor of FIG. 1.

The present disclosure is directed toward a gas sensor, and more specifically, a gas sensor for detecting carbon dioxide and other gases, and in some cases, humidity, in a gas sample. FIG. 1 is a cross-sectional side view of one illustrative gas sensor. FIG. 2 is a schematic top view of the illustrative gas sensor of FIG. 1. The illustrative gas sensor is generally shown at 10, and includes a sensor 12 formed on or above a substrate 14. The illustrative sensor 12 includes a heater layer 16, a buffer layer 18, a lower electrode layer 20, a solid electrolyte layer 22, and an upper electrode layer 24, as best shown in FIG. 1. It should be understood that the specific layers shown, as well as their relative positions, may be changed and still be within the scope of the present invention. All that is important is that the heater layer 16 is thermally coupled to the solid electrolyte layer 22, and contacts are provided from the solid electrolyte layer 22.

In the illustrative embodiment, the heater layer 16 is made from a resistive material that generates heat when a current is passed therethrough. To increase the heat the can be delivered to the sensor 12, as well as the uniformity of the heat, the heater layer 16 may be configured to meander back and fourth along the area of the sensor 12, as better shown in FIG. 2.

In the illustrative embodiment, the solid electrolyte layer 22 may be made from a suitable solid electrolyte material. For example, if the gas to be detected is $CO_2$ and/or humidity, the solid electrolyte may be lanthanum oxide, $La_2O_3$ (CAS No.: 1312-81-8) available from Sigma Aldrich Chemical Company, Milwaukee Wis. The solid electrolyte layer 22 can be a layer of $La_2O_3$ or a layer of material (such as silica, for example) doped with $La_2O_3$, as desired.

Lanthanum oxide is a useful solid electrolyte since it absorbs water and carbon dioxide at ambient temperature and desorbs water as it is heated to 100 degrees Celsius and then desorbs carbon dioxide as it is heated above 100 degrees Celsius. As such, a single heating cycle of the gas sensor can provide accurate concentration measurements of both water (e.g., humidity) and carbon dioxide in a gas sample. With the physical properties (i.e., specific absorption capacity, volume, and mass) of lanthanum oxide and the amount of heat applied to lanthanum oxide, a concentration of both water and carbon dioxide can be determined based on the change in thermal mass with differential thermal analysis. One illustrative differential thermal analysis sensor is described in U.S. Pat. No. 6,238,085, and is incorporated by reference herein. In one illustrative embodiment, the gas sensor has an ultimate carbon dioxide sensitivity of 5 ppm.

Control electronics 28 may be provided on or in the substrate 14, or elsewhere, as desired. Control electronics 28 can be coupled to the heater layer 16 via traces 30a and 32b, and the lower electrode layer 20 and the upper electrode layer 24 via traces 32a and 32b, as best shown in FIG. 2. During operation, control electronics 28 can provide power to the heater layer 16 to heat the sensor 12 to an operating temperature, which is above an ambient temperature. The application of heat to the sensor 12, and more specifically, to the solid electrolyte layer 22, causes the absorbed gases to desorb.

Figure 4:
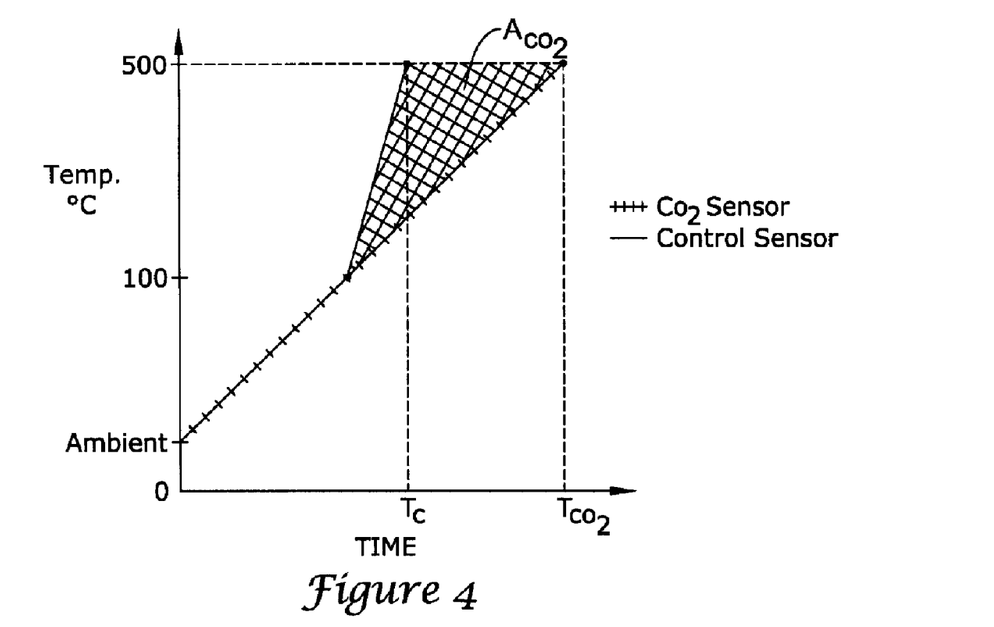
FIG. 4 is a time verses temperature graph showing differential thermal analysis for determining a concentration of carbon dioxide in a gas sample.

Referring to FIG. 4, and in one illustrative embodiment, the control electronics 28 may provide power to the heater layer 16 to heat the sensor to the operating temperature during a first period of time with a first amount of energy. FIG. 4 shows an illustrative time verses temperature graph of a control sensor and a $CO_2$ sensor according to the present disclosure. At time zero, the sensors are at ambient temperature. Energy (i.e., current) is applied to both sensors at a constant rate and at a constant voltage, thus providing a constant power to the heater. Both sensors reach 100 degrees Celsius at about the same time, with about the same amount of energy (which can be calculated by integrating the area under each curve.) At 100 degrees Celsius, carbon dioxide begins to desorb from the $CO_2$ sensor, causing the $CO_2$ sensor to heat up at a slower rate than the control sensor. At time equal to $T_C$, the control sensor reaches a temperature of 500 degrees Celsius. At time equal to $T_{CO2}$, the $CO_2$ sensor reaches a temperature of 500 degrees Celsius. At a temperature of about 500 degrees Celsius substantially all of the carbon dioxide has desorbed from the sensor. The difference in the areas under each curve ($A_{CO2}$) corresponds to the amount of energy required to desorb the carbon dioxide from the sensor. Knowing the physical properties of the solid electrolyte and carbon dioxide, a total amount of carbon dioxide desorbed from the sensor can be determined. A concentration of carbon dioxide in the gas sample can then be determined based on known equilibrium constants of carbon dioxide and the solid electrolyte at ambient absorption temperature and pressure.

Figure 5:
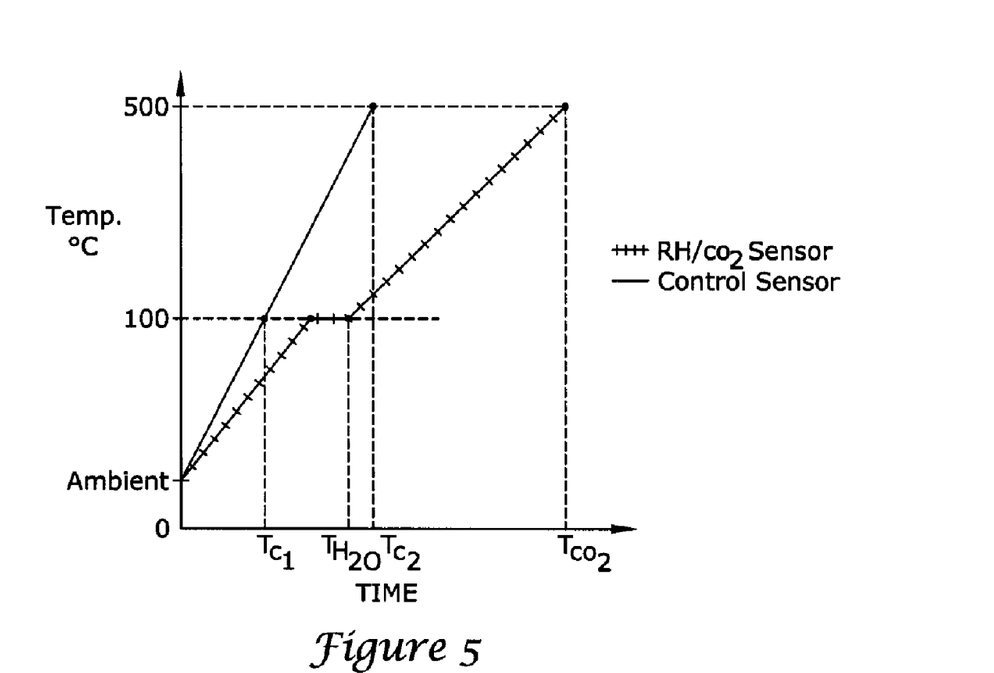
FIG. 5 is a time verses temperature graph showing differential thermal analysis for determining a concentration of water and carbon dioxide in a gas sample.

FIG. 5 shows an illustrative time verses temperature graph of a control sensor and a relative humidity (RH) and $CO_2$ sensor according to the present disclosure. At time zero, the sensors are at ambient temperature. Power (i.e., current/voltage) is applied to both sensors at a constant rate. Here, the $RH/CO_2$ sensor reaches and begins to rise above 100 degrees Celsius at time equal to $T_{H2O}$, and the control sensor reaches 100 degrees Celsius at time equal to $T_{C1}$. The difference in the total amount of energy required for each sensor to reach and just exceed 100 degrees Celsius is related to the amount of water that desorbed from the $RH/CO_2$ sensor. Knowing the physical properties of the solid electrolyte and water, a total amount of water desorbed from the sensor can be determined. A concentration of water in the gas sample can then be determined based on known equilibrium constants of water and the solid electrolyte at ambient absorption temperatures and pressures. Relative humidity can then be determined using known techniques.

Above 100 degrees Celsius, carbon dioxide begins to desorb from the $RH/CO_2$ sensor, causing the $CO_2$ sensor to heat up at a slower rate than the control sensor. At time equal to $T_{C2}$, the control sensor reaches a temperature of 500 degrees Celsius. At time equal to $T_{CO2}$, the $CO_2$ sensor reaches a temperature of 500 degrees Celsius. At a temperature of about 500 degrees Celsius substantially all of the carbon dioxide has desorbed from the sensor. The difference in the areas under each curve (above 100 degrees Celsius) is the amount of energy required to desorb the carbon dioxide from the sensor. Knowing the physical properties of the solid electrolyte and carbon dioxide, a total amount of carbon dioxide desorbed from the sensor can be determined. A concentration of carbon dioxide in the gas sample can then be determined based on known equilibrium constants of carbon dioxide and the solid electrolyte at ambient absorption temperatures and pressures.

In some embodiments, a control sensor may, or may not, be provided. The control sensor can be identical in construction to the gas sensor without the lanthanum oxide. The control sensor can be coupled to the controller and provide a control heating profile for the gas sensor. Thus, a differential heating profile, or differential energy amount can be determined and used to determine desorbed carbon dioxide and/or humidity from the gas sensor. When a control sensor is not provided, the desorbed carbon dioxide and/or humidity can be determined from calculated sensor characteristic data previously known or determined and may be stored in a memory within the controller.

In some embodiments, the sensor 12 may be thermally isolated from some or all of the remainder of the gas sensor 10. In the embodiment shown in FIG. 1, a pit 52 may be etched into the substrate below the sensor 12 leaving a gap or space between the sensor 12 and the substrate 14. The gap may be an air gap, or filled with a material with a low coefficient of thermal conductivity. Supporting legs 50a-d may be left in tact to support the sensor 12 above the pit 52. In this configuration, the sensor 12, which includes the heater 16 and the solid electrolyte layer 22, is suspended above the substrate, which helps thermally isolate the sensor 12 from the remainder of the gas sensor 10. This may help reduce the amount of power and time that is required to heat the sensor 12 to the operating temperature.

Because the amount of power required to heat the sensor 12 to the operating temperature is reduced, and/or because the sensor 12 is only heated when a reading is desired, the gas sensor 10 may be suited for battery powered and/or wireless applications. For example, the control electronics 28 may be powered by a battery 56, and/or the control electronics 28 may wirelessly transmit an output signal from the gas sensor 10 via an antenna 58.

Figure 3:
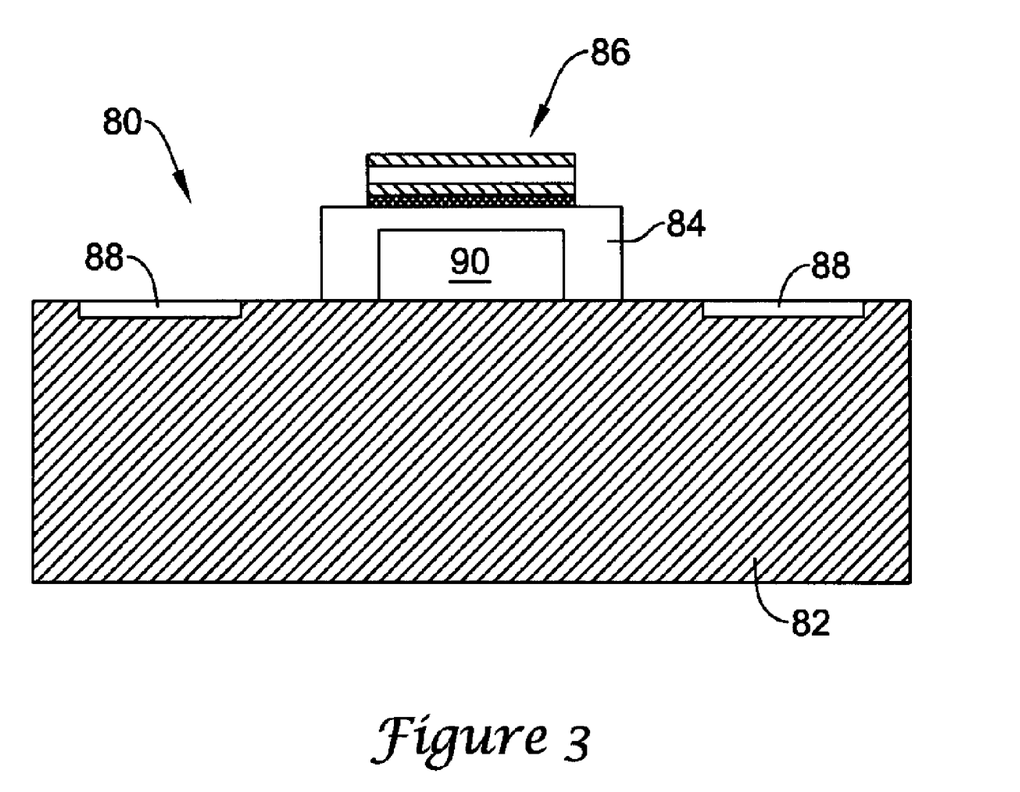
FIG. 3 is a cross-sectional side view of another illustrative gas sensor in accordance with the present invention.

FIG. 3 is a cross-sectional side view of another illustrative gas sensor in accordance with the present invention. The illustrative gas sensor is generally shown at 80, and includes a substrate 82, a support structure 84, a sensor 86 and control electronics 88. This embodiment is similar to that shown and described above with respect to FIGS. 1-2. However, rather than suspending the sensor above an etched pit 52 in the substrate, as shown in FIG. 1, a support structure is provided on the substrate that suspends the sensor 86 above the substrate 82. A gap 90 or the like may be provided below the support structure 84 to help provide thermal isolation. Alternatively, or in addition, the support structure 84 may be formed from a material that has a low coefficient of thermal conductivity. Regardless of which approach is used, the sensor 10 and sensor 86 may be relatively thermally isolated from the substrate.

Figure 6:
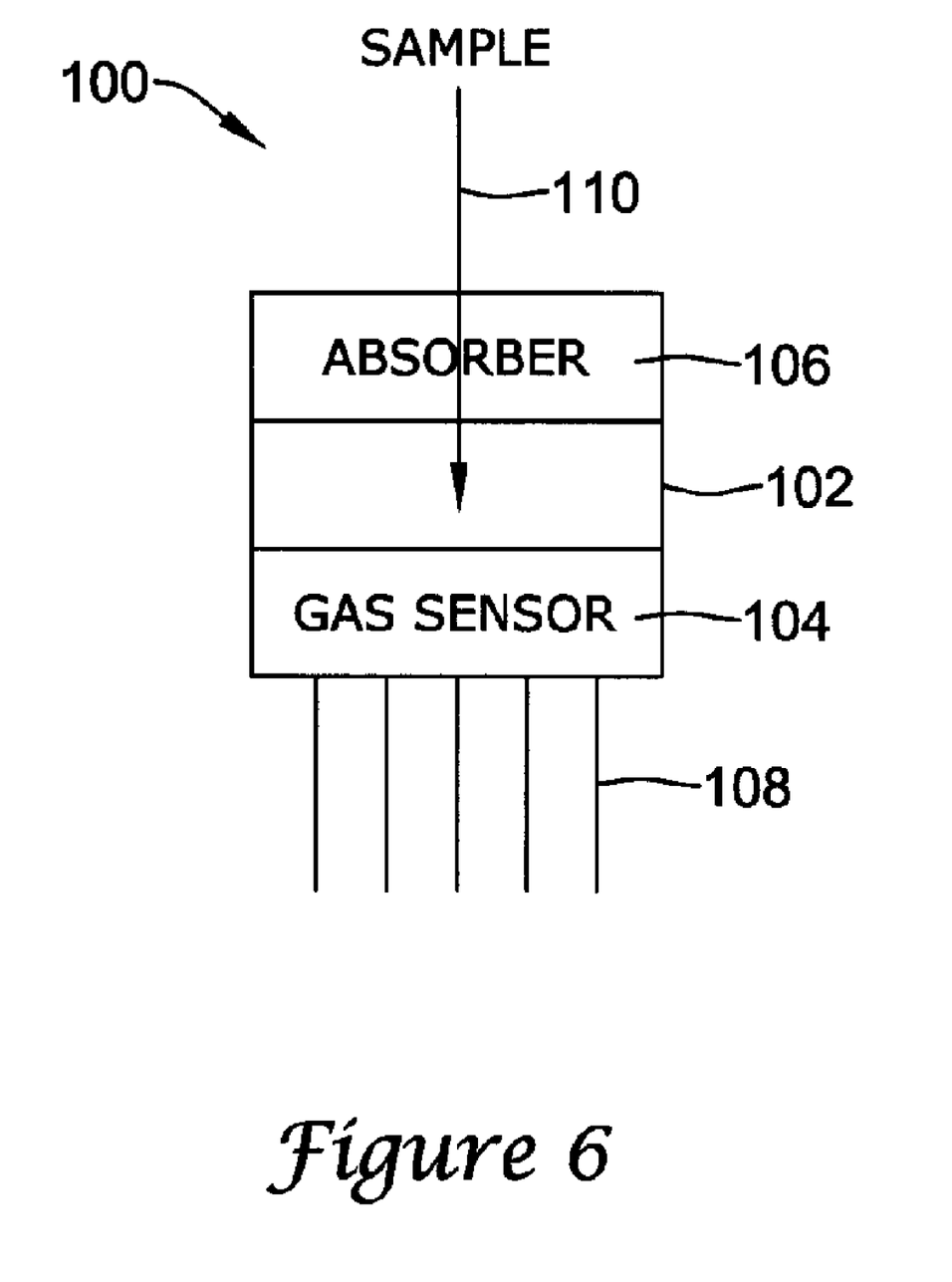
FIG. 6 is a schematic side view of an illustrative gas sensor assembly in accordance with the present invention.

FIG. 6 is a schematic side view of an illustrative gas sensor assembly in accordance with the present invention. The gas sensor assembly is generally shown at 100, and includes a housing 102, a gas sensor 104, and an absorber 106. The gas sensor may be similar to those shown and described above with respect to FIGS. 1-5.

A gas sample 110 from an environment may be provided to the gas sensor 104 through the absorber 106. The absorber may include an absorbent material that absorbs unwanted constituents or gases from the sample 110 before the sample 110 reaches the gas sensor 104. For example, the absorber may absorb one or more interference gases. In some cases, interference gases can reduce the reliability or accuracy of the measurements made by the gas sensor 104.

The gas sensor assembly 100 may further include a number of leads 108. The leads 108 may provide a mechanical and/or electrical connection between the gas sensor assembly 100 and an external board or the like, when desired.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method for sensing a gas, the method comprising the steps of:

providing a solid electrolyte layer comprising lanthanum oxide;

contacting the solid electrolyte layer with a gas sample;

heating the solid electrolyte layer from about 100 degrees Celsius to an operating temperature with a first amount of energy; and determining a concentration of carbon dioxide in the gas sample based on first amount of energy.

2. A method according to claim 1 wherein the providing step comprises fixing the solid electrolyte layer relative to, but spaced from, a substrate.

3. A method according to claim 1 wherein the providing step comprises suspending at least part of the solid electrolyte layer above the substrate.

4. A method according to claim 1 further comprising heating the solid electrolyte layer from an ambient temperature to about 100 degrees Celsius with a second amount of energy.

5. A method according to claim 4 further comprising the step of determining a relative humidity level in the gas sample based on the second amount of energy provided to the solid electrolyte layer.

6. A method according to claim 1 wherein the heating step comprises heating the solid electrolyte layer from about 100 degrees Celsius to about 500 degrees Celsius with the first amount of energy.

7. A method according to claim 6 further comprising the step of determining a concentration of carbon dioxide in the gas sample based on the first amount of energy provided to the solid electrolyte layer.

8. A method for determining a humidity level and a concentration of carbon dioxide in a gas sample, the method comprising the steps of:

providing a solid electrolyte layer comprising lanthanum oxide;

contacting the solid electrolyte layer with a gas sample;

heating the solid electrolyte layer to about 100 degrees Celsius with a water desorbing amount of energy;

heating the solid electrolyte layer from about 100 degrees Celsius to a carbon dioxide desorbing temperature with a carbon dioxide desorbing amount of energy; and determining a humidity level in the gas sample based on the water desorbing amount of energy and determining a concentration of carbon dioxide in the gas sample based on the carbon dioxide amount of energy.

9. A method according to claim 8 wherein the providing step comprises fixing the solid electrolyte layer relative to, but spaced from, a substrate.

10. A method according to claim 8 wherein the providing step comprises suspending at least part of the solid electrolyte layer above the substrate.

11. A method according to claim 1 wherein the heating step of heating the solid electrolyte layer from about 100 degrees Celsius to a carbon dioxide desorbing temperature with a carbon dioxide desorbing amount of energy comprises heating the solid electrolyte layer from about 100 degrees Celsius to about 500 degrees Celsius with a carbon dioxide desorbing amount of energy.

\* \* \* \* \*

UNITED STATES PATENT AND TRADEMARK OFFICE
CERTIFICATE OF CORRECTION

PATENT NO. : 7,628,907 B2 Page 1 of 1
APPLICATION NO. : 11/162060
DATED : December 8, 2009
INVENTOR(S) : Gu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1139 days.

Signed and Sealed this

Second Day of November, 2010

David J. Kappos
*Director of the United States Patent and Trademark Office*